United States Patent [19]

Stark

[11] Patent Number: 4,658,131
[45] Date of Patent: Apr. 14, 1987

[54] INTEGRATING SPHERE UTILIZING A POSITIVE POWER LENS

[75] Inventor: Edward W. Stark, Yorktown Heights, N.Y.

[73] Assignee: Technicon Instruments Corporation, Tarrytown, N.Y.

[21] Appl. No.: 470,234

[22] Filed: Feb. 28, 1983

[51] Int. Cl.[4] .......................... G01J 1/04; G01N 21/01
[52] U.S. Cl. ..................................... 250/228; 356/236
[58] Field of Search ................. 250/228, 338 R, 341; 356/215, 236, 432, 435, 246

[56] References Cited

U.S. PATENT DOCUMENTS

| | | | |
|---|---|---|---|
| 2,280,993 | 4/1942 | Barnes | 356/236 |
| 2,364,825 | 12/1944 | Shurcliff | 356/236 |
| 4,278,887 | 7/1981 | Lipshutz et al. | 356/236 |

Primary Examiner—Edward P. Westin
Attorney, Agent, or Firm—James J. Romano, Jr.; James R. Cartiglia

[57] ABSTRACT

A lens for utilization in the radiation energy exit port of a radiation energy integrating sphere is provided, and functions to prevent instrumental specular radiation energy reflections from striking the interior wall surfaces of the sphere and being collected thereby. The instrumental specular radiation energy reflections include those from the lens, per se, and those from instrumentation disposed without the integrating sphere.

13 Claims, 4 Drawing Figures

INTEGRATING SPHERE UTILIZING A POSITIVE POWER LENS

BACKGROUND OF THE INVENTION

1. Field of the Invention

This invention relates to an improvement taking the form of lens means in radiation energy integrating spheres as used, for example, though by no means exclusively, in spectroscopic quantitative sample analysis systems.

2. Description of the Prior Art

The use of radiation energy integrating spheres in, for example, spectroscopic quantitative sample analysis systems, is known in the prior art to give rise to the problem of collection by the integrating sphere of the instrumental, i.e., instrument generated, specularly—and non sample information-bearing—reflected radiation energy from the viewing windows of the sphere and sample cell, with attendant reduction in sample analysis accuracy. The prior art solutions to this problem generally involve either the enlargement of the radiation energy entry port of the integrating sphere to an extent sufficient to enable substantially all of the instrumental, specularly reflected radiation energy to exit the sphere therethrough without impingement on the interior wall surfaces of the sphere, and/or the masking of the interior wall surfaces of the sphere adjacent a radiation energy entry port of the minimum optically required size to an extent sufficient to absorb substantially all of the instrumental, specularly reflected radiation energy. In each instance, these solutions, although generally satisfactory with regard to preventing the collection of the instrumental, specularly reflected radiation energy by the integrating sphere, significantly reduce the amount of the internal surface area of the integrating sphere which can operate to collect the sample information-bearing diffusely reflected radiation energy of interest, with attendant significant reduction in the optical gain of the integrating sphere and thus in the overall accuracy of the sample analysis process.

Austrian Pat. No. 218277 discloses the reduction or elimination of artifacts in optical sample analysis systems. In those systems, however, the sample-containing sphere is not an integrating sphere, and no lens means are utilized to the above purposes.

U.S. Pat. No. 4,310,249 discloses the use of an integrating sphere in conjunction with a cylindrical sample container that can behave like a cylindrical lens. No means are included in this disclosure to discriminate between specularly, as opposed to diffusely, reflected radiation energy to improve sample analysis accuracy.

U.S. Pat. Nos. 3,515,489, 3,554,650 and 3,827,811 respectively disclose optical systems comprising reflective elements and lenses. No means are disclosed in any of these systems to discriminate between specularly, as opposed to diffusely, reflected radiation energy for any purposes.

OBJECTS OF THE INVENTION

It is, accordingly, an object of this invention to provide new and improved lens means for use in radiation energy integrating spheres of optical sample analysis systems.

Another object of the invention is the provision of new and improved lens means as above which increase the optical gain of the integrating sphere and, accordingly, the accuracy of the sample analysis systems.

Another object of the invention is the provision of lens means as above which reduce the maintenance requirements of the integrating spheres.

Another object of this invention is the provision of lens means as above which are of relatively simple and inexpensive configuration.

Another object of this invention is the provision of lens means as above which are particularly adapted for use in radiation energy integrating spheres as form part of spectroscopic quantitative sample analysis systems.

SUMMARY OF THE INVENTION

As disclosed herein, the preferred embodiment of the invention comprises lens means which are operatively disposed in the radiation energy exit port of a radiation energy integrating sphere and which are operable to prevent instrumental specular reflections from outside the integrating sphere of radiation which has been transmitted through the integrating sphere from striking the interior wall surfaces of the integrating sphere upon re-entry into the integrating sphere through the radiation energy exit port. In addition, the lens means are effective to prevent instrumental specular reflections from the lens means surfaces of the sphere-transmitted radiation energy from striking the integrating sphere interior wall surfaces. The integrating sphere incorporating the lens means of the invention find particularly useful application in spectroscopic quantitative sample analysis systems which include a sample cell having a flat sample viewing window and wherein the specular radiation energy reflections from the sample viewing window and the lens means, which contain no information relevant to sample analysis, are prevented by the lens means from striking the interior wall surfaces of the integrating sphere and degrading the sample analysis accuracy, all without loss in the optical gain of the integrating sphere.

DESCRIPTION OF THE DRAWINGS

The above and other objects and advantages of the invention are believed made clear by the following detailed description of a preferred embodiment thereof taken in conjunction with the accompanying drawings wherein.

DETAILED DESCRIPTION OF A PREFERRED EMBODIMENT

Figure 1:
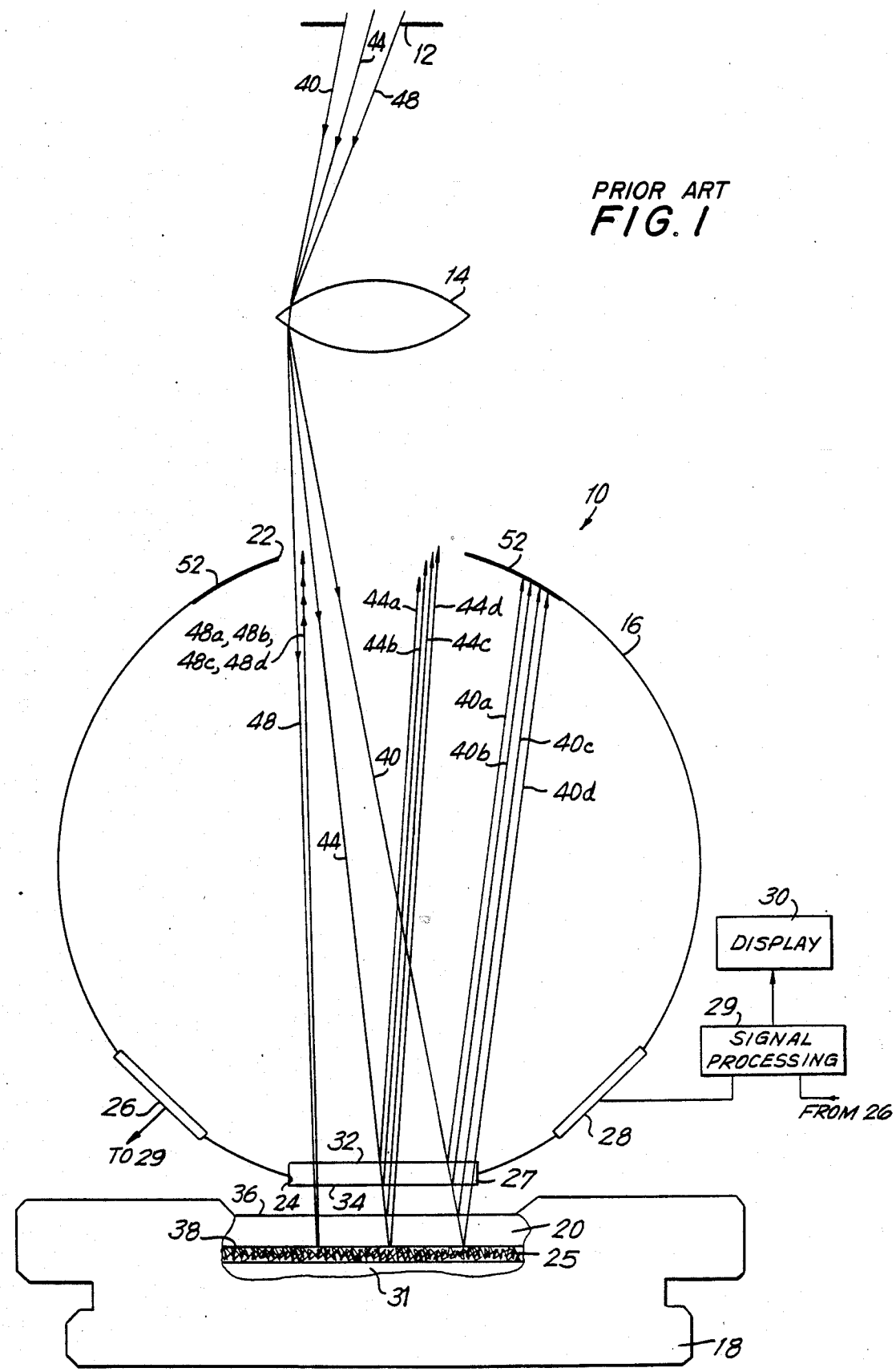
FIG. 1 is a diagramatic view of an optical sample analysis system incorporating an integrating sphere configured and operable in accordance with the principles of the prior art.

Referring now to FIG. 1, a representative spectroscopic quantitative sample analysis system of the prior art is indicated generally at 10, and will be seen to comprise an aperture 12 illuminated by a radiation energy source (not shown) an objective lens 14, a radiation energy integrating sphere 16, and a sample cell 18 having a flat sample viewing window 20. The integrating sphere 16 comprises radiation energy entry and exit ports 22 and 24, with the latter including a flat viewing window 27; and the system 10 is arranged so that the aperture source 12, objective lens 14, entry and exit ports 22 and 24, and sample viewing window 20 are respectively optically aligned as shown. In use of the system 10 for quantitative sample analysis, radiation energy from aperture 12 at different wavelengths— predetermined in accordance with the spectral reflectance characteristics of the sample, and the particular sample constituents(s) of interest—is focussed by lens 14 through integrating sphere entry and exit ports 22 and 24, and viewing window 27, to sequentially irradiate the sample 25 in sample cell 18 through viewing window 20. The diffusely reflected radiation from the sample 25 re-enters the integrating sphere 16 through viewing window 27 in exit port 24 and is collected within the former to impinge upon radiation collectors as representatively depicted at 26 and 28; and the level of the thusly collected radiation is applied as shown to signal detecting and processing means 29 and display means 30 for computation and display of the concentration(s) of the particular sample constituents(s) of interest, generally in accordance with the attenuation of the radiation energy which is transmitted through the sample 25 and diffusely reflected back through the sample by a diffuse reflector 31 which forms the back of the sample cup 18, and the attenuation of the radiation energy which is diffusely reflected within the sample, per se. A spectroscopic analysis system of this nature is disclosed in detail in U.S. Pat. No. 4,278,887 issued July 14, 1981 to Victor G. Lipshutz and Edward Stark, and assigned to the assignee hereof; and the disclosure of that patent is incorporated by reference herein.

A problem in the operation of sample analysis systems of this nature arises from the fact that sample analysis accuracy can be significantly degraded by the Fresnel reflections of the radiation energy which, of necessity, occur at the dissimilar index of refraction interfaces 32, 34, 36 and 38 of the outer and inner surfaces of the integrating sphere and sample cup viewing windows 27 and 20, and the ambient air and sample 25, respectively. More specifically, this instrumental, specularly reflected and non sample information-bearing, radiation energy will diffuse throughout the integrating sphere 16 upon re-entry thereinto through exit port 24; with those components thereof—as representatively depicted by specularly reflected rays 40a, 40b, 40c and 40d, respectively, of the steepest radiation energy ray 40 from objective lens 14—which do not exit the integrating sphere 16 through inlet port 22 striking the interior wall of the integrating sphere 16 as shown in the general area of the inlet port and being collected as described within the integrating sphere for ultimate impingement upon collectors 26 and 28 and resultant addition by signal processing means 29 to the detected level(s) of diffusely reflected radiation energy for the sample of interest. Thus, falsely low radiation energy attenuation by diffuse reflection from the sample 25 and diffuse reflector 31 would be detected and processed by the signal processing means 29, with attendant less than optimal accuracy of the sample analysis results. Although, for completeness of illustration the center ray 44, and the least steep ray 48, and the associated specularly reflected rays 44a, 44b, 44c and 44d, and 48a, 48b, 48c and 48d, respectively, of the radiation energy from objective lens 14 are shown in FIG. 1; it will be clear that since the instrumental Fresnel reflections thereof exit the sphere 16 through entrance port 22, the same do not contribute to the problem under discussion.

Calibration of the sample analysis system 10 to correct for this adverse phenomenon has not proven fully satisfactory and is, in any event, rendered particularly difficult by the fact that calibration accuracy varies in accordance with variation in the wavelength of sample radiation.

A common prior art solution to this problem resides in the masking of the interior wall surface of the integrating sphere 16 by a suitable radiation energy absorbing material as indicated at 52 in FIG. 1 to an extent sufficient to insure the absorption, and thus prevent the collection, within the integrating sphere 16 of all of the instrumental specularly reflected radiation energy under discussion. Alternatively, the size of the radiation energy entry port 22 is enlarged in the prior art, not shown, to an equivalent extent of the masking beyond that minimum port size as dictated by the spread of the least steep radiation energy rays 48 from objective lens 14, to insure that the steepest rays of the instrumental specularly reflected radiation energy 40a, 40b, 40c and 40d exit the sphere through the entry port and are thus not collected by the former for detection and processing. A further prior art alternative, not shown, resides in a combination of the above, i.e., a more moderate enlargement of the radiation energy entry port 22 and masking of the remaining interior wall surface of interest of the integrating sphere. However, all of the above solutions significantly reduce the interior wall surface are of the integrating sphere 16 which is available for reflected, sample information-bearing radiation energy collection with attendant significant reduction in the optical gain of the integrating sphere and, accordingly, in the accuracy of sample analysis results. In addition, any enlargement of the sphere radiation energy entry port 22 adds materially to the maintenance requirements of the integrating sphere.

Figure 2:
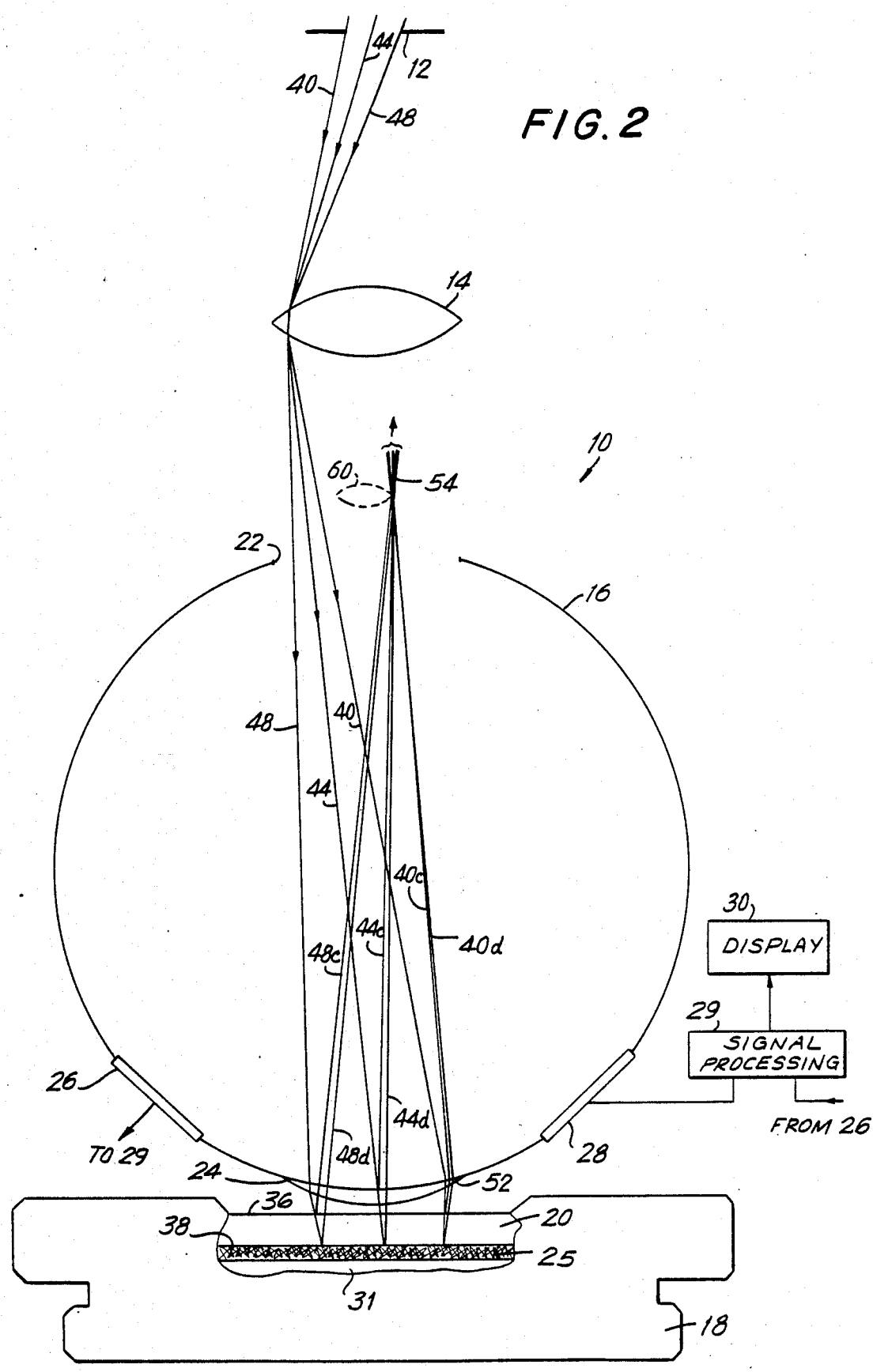
FIGS. 2, 3 and 4 are respectively diagramatic views of the optical sample analysis system of FIG. 1 incorporating an integrating sphere configured and operable in accordance with the teachings of this invention.
Figure 3:
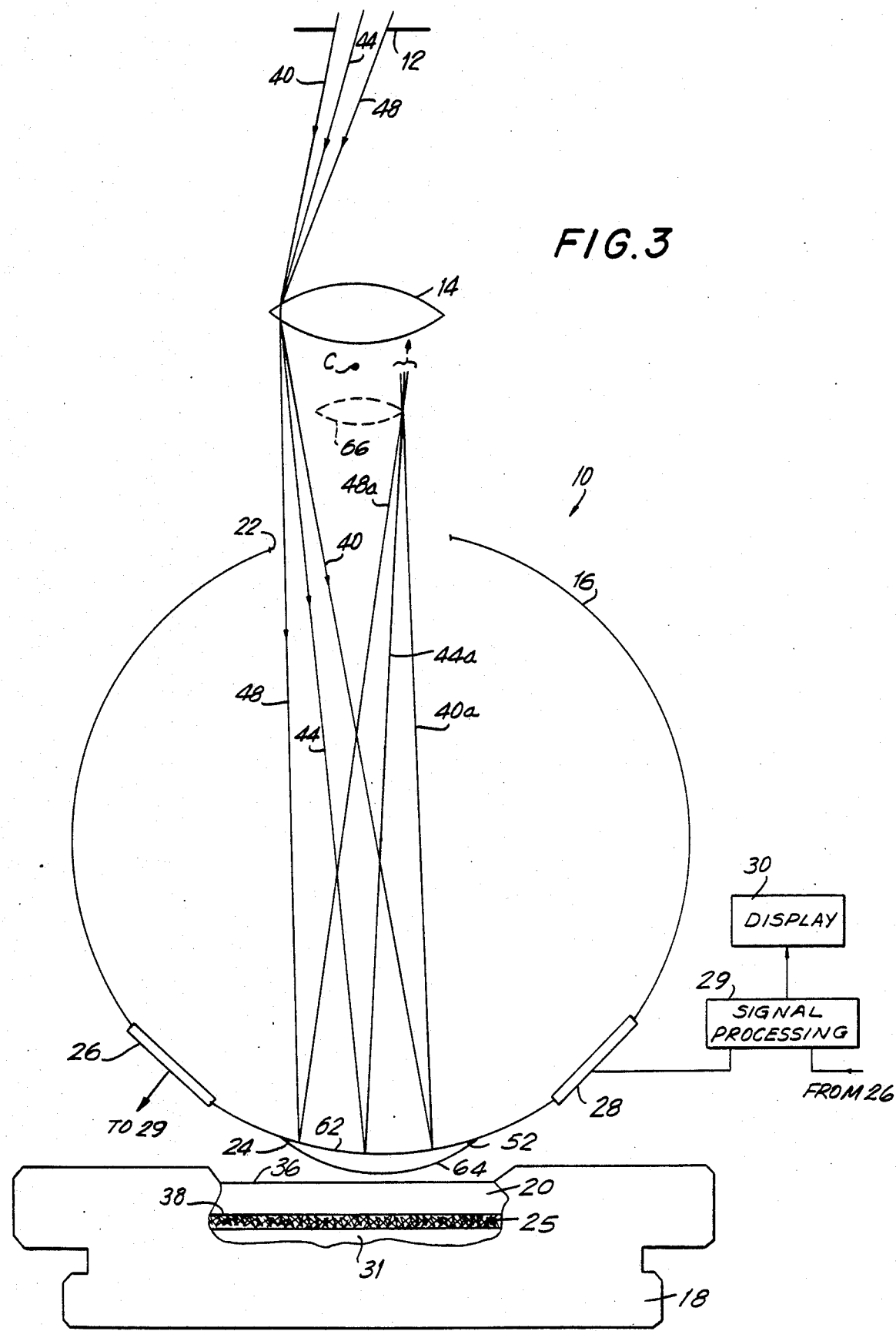
Figure 4:
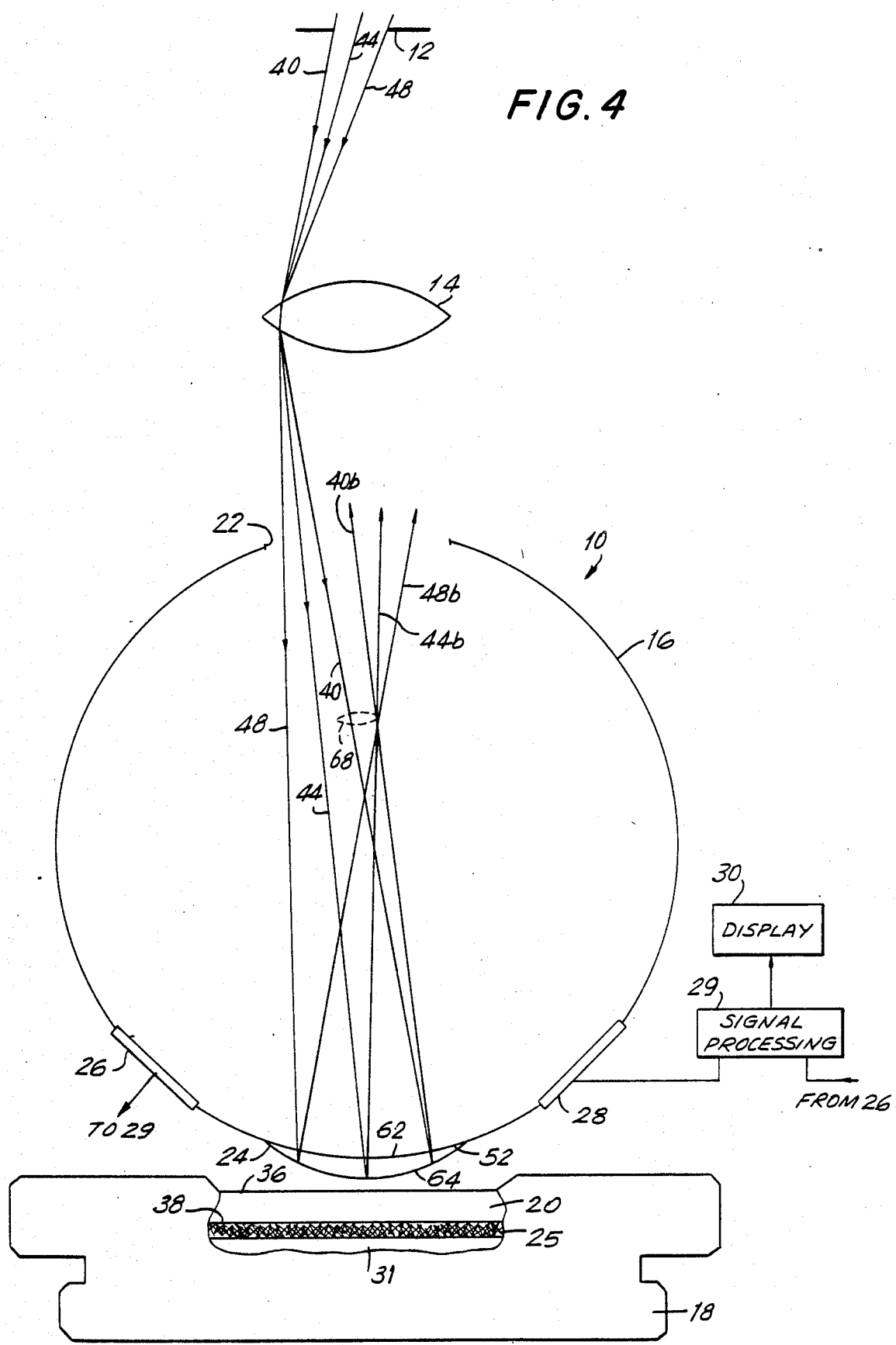

A particularly novel and effective solution to this problem, and one which does away with the necessity for enlargement of the radiation energy entry port 22 beyond that minimum size dictated by the beam width of the least deviated radiation energy rays 48 and/or the masking as at 52 in FIG. 1 of the interior wall surface of the integrating sphere 16 adjacent that entry port, has now been determined in accordance with the teachings of this invention to reside in the replacement as shown in FIGS. 2, 3 and 4 in the integrating sphere radiation energy exit port 24, of the flat viewing window 27— which is not a lens in that it does not re-direct radiation energy—by a lens 52 of appropriate optical characteristics. As clearly shown in FIGS. 2, 3 and 4, lens 52 is thicker at the center than at the edges and comprises lens faces of different radii of curvature, thus making clear that the lens is of positive power. Lens 52 is optically configured to control the beam width(s) and ultimate orientation(s) of the instrumental, non sample information-bearing specularly reflected radiation energy, while nonetheless advantageously retaining a flat sample cup viewing window 20, so that this specularly reflected radiation energy will exit the integrating sphere 16 through an optically minimal sized entry port 22 and is thus not detected and processed for inclusion in the sample analysis results.

More specifically, and as representatively illustrated in FIG. 2, the lens power of lens 52 is designed to deviate and collimate the steepest radiation energy rays 40 from objective lens 14 prior to the impingement thereof on sample cup viewing window interfaces 36 and 38, to deviate the specular reflections 40c and 40d of those rays from those interfaces, to deviate and collimate the least steep radiation rays 48 prior to impingement thereof on sample cup viewing window interfaces 36 and 38, to deviate the specular reflections 48c and 48d of those rays from those interfaces, and to leave substantially undeviated the center rays 44 and the specular reflections 44c and 44d thereof from interfaces 36 and 38, respectively; all to form bundle 54 of specularly reflected radiation energy rays which leave the integrating sphere 16 by radiation energy entry port 22 for reimaging of the objective lens 14 outside of the integrating sphere as representatively indicated in dashed lines at 60. Thus, the instrumental, specularly reflected radiation energy from the sample cup viewing window is totally prevented from striking the interior wall surfaces of the integrating sphere 16, whereby the accuracy of the sample analysis results is in no way adversely affected thereby.

Of course, the placement as described of the lens 52 in the radiation energy exit port 24 of the integrating sphere 16 gives rise to instrumental, lens-generated Fresnel reflections of radiation energy at the respective interior and exterior lens surface-ambient air interfaces 62 and 64 shown in FIG. 3, it being clear that this specularly reflected radiation energy must also be prevented from striking the interior wall surfaces of the integrating sphere 16 and thus adversely affecting the accuracy of the sample analysis results.

To this effect, and considering initially the radiation energy from objective lens 14 which is instrumentally specularly reflected from interior lens-air interface 62, FIG. 3 makes clear that the curvature of the interior lens surface is designed in conjunction with the lens power so that the center of curvature C of this lens surface is near the objective lens 14, whereby the latter will be essentially reimaged, in reduced size, almost upon itself outside the integrating sphere 16 as indicated in dashed lines 66. This is representatively illustrated in FIG. 3 by the specularly reflected radiation energy ray 40a from interface 62 of the lens curvature-controlling steepest radiation energy ray 40 from objective lens 14, the specularly reflected radiation energy ray 48a from interface 62 of the least steep radiation energy ray 48 from the objective lens, and the specularly reflected radiation energy ray 44a from interface 62 of the center radiation energy ray 44 from the objective lens, which may respectively be seen to be re-directed by reflection from the lens-air interface 62 of interest to leave the integrating sphere 16 by radiation energy entry port 22 for reimaging of the objective lens 14 as described at 66. Thus, none of this interior lens surface-air interface reflected radiation energy strikes the interior wall surfaces of the integrating sphere 16.

Regarding the radiation energy which is specularly reflected from exterior lens surface-air interface 64 as illustrated in FIG. 4, it may be understood that the curvature of the exterior lens surface is designed, in conjunction with the index of refraction and power of lens 52, to in essence form a Mangin mirror of relatively short focal length which operates to reimage objective lens 14 in reduced size as indicated in dashed lines at 68, within the integrating sphere 16 in optical alignment with radiation energy entry port 22. This is representatively illustrated in FIG. 4, again by the specularly reflected radiation energy ray 40b from interface 64 of the steepest radiation energy radiation ray 40 from objective lens 14, the specularly reflected radiation energy ray 48b from interface 64 of the least steep radiation energy ray 48 from objective lens 14, and the specularly reflected radiation energy ray 44b from interface 64 of the center radiation energy rays 44 and from the objective lens, which may respectively be seen to be deviated by both lens surface-air interfaces 62 and 64, through the combined power of lens 52 and the curvature of exterior lens surface 64, to reimage the objective lens 14 as illustrated at 68. Again, none of this lens-reflected radiation energy strikes the interior wall surfaces of the integrating sphere 16; whereby adverse effect upon sample analysis accuracy by instrumental specularly reflected radiation energy from the respective interior and exterior lens surface-air interfaces 62 and 64 is positively prevented.

Of course, FIGS. 2, 3 and 4 depict radiation energy ray reflection conditions which occur concomitantly attendant the use of the lens 52 of the invention in the illustrated sample analysis system environment; which conditions are depicted in separate drawing figures only for convenience and clarity of ray illustration. In practice, lens 52 is designed to simultaneously control rays 40d, 40a and 40b so as to minimize the required size of entry port 22, considering also ray 48 from lens 14.

Although effective as described to focus instrumental specularly reflected, non sample information-bearing radiation energy, it is clear that lens 52 will have no significant effect upon the diffusely reflected, sample information-bearing radiation energy of interest from sample analysis cup 18, although the diffusely reflected energy distribution will be modified.

The specularly reflected radiation focussing capability as described of lens 52 makes possible the use of the minimally sized radiation energy entry port 22 commensurate with the satisfactory admission of radiation energy from aperture 12 through objective lens 14, as determined by the beam width of the least steep radiation energy rays 48, for irradiation of a suitable area of the sample 25 through viewing window 20. In addition, the need for masking of the interior wall surface of the integrating sphere 16 adjacent this minimally sized radiation energy entry port is totally eliminated. These factors, in turn, enable the use of a proportionally greater part of the internal surface area of the integrating sphere 16 for sample information-bearing radiation collection, thus increasing the optical gain and accordingly the optical efficiency of the integrating sphere. In addition, this lens focussing capability can enable the precise irradiation of a maximal sample surface area, with attendant maximal energy throughout for the sample analysis system. This provides a braoder based average for the sample constituent(s) of interest, which is particularly significant in the quantitative analysis of non-homogeneous samples, and increases the signal to noise ratio of the sample analysis system 10 thereby, in both instances, contributing materially to increased sample analysis accuracy. Also, the minimization in size of the radiation enerby entry port 22, taken in conjunction with the continued closure of the radiation energy exit port 24 by the lens 38, materially inhibit the contamination of the interior wall surfaces of the integrating sphere 16 by ambient air-borne dust or the like, thus significantly reducing the requirement for periodic cleaning of the integrating sphere to maintain the optical efficiency thereof at maximal level, Further, although calibration of the sample analysis system 10 incorporating the lens 38 would still be required, it will be clear to those skilled in this art that the teachings of this invention will render calibration and correction far less complex or critical.

Various changes may be made in the disclosed embodiment of the invention without departing from the spirit and scope thereof as defined in the appended claims.

What is claimed is:

1. In a radiation energy integrating sphere which includes optically aligned radiation energy entry and exit ports for the transmission of radiation energy through the sphere, the improvements comprising, lens means operatively associated with said radiation energy exit port, said lens means being of positive power and operable to prevent specular reflections from the lens means surfaces of radiation energy which has been transmitted into said integrating sphere through said radiation energy entry port from striking the interior wall surfaces of said integrating sphere for collection thereby.

2. In a radiation energy integrating sphere as in claim 1 wherein, said lens means are disposed in said radiation energy exit port.

3. In a radiation energy integrating sphere as in claim 1 wherein, said lens means are operable to direct said specular reflections of said radiation energy out of the integrating sphere through said radiation energy entry port.

4. In a radiation energy integrating sphere as in claim 1 wherein, said lens means are disposed in said radiation energy exit port and comprise an interior lens means surface and exterior lens means surface, with the curvature of said interior lens means surface being operable to direct specular reflections of said radiation energy from said interior lens means surface out of the integrating sphere through said radiation energy entry port, and the curvature of said exterior lens means surface, the index of refraction of said lens means and the power of said lens means being operable to form a Mangin mirror to direct specular reflections of said radiation energy from said exterior lens means surface out of the integrating sphere through said radiation energy entry port.

5. In a radiation energy integrating sphere for use in a sample analysis system and including optically aligned radiation energy entry and exit ports for the transmission of radiation energy through the sphere, the improvements comprising, lens means operatively associated with said radiation energy exit port, said lens means being of positive power and operable to prevent instrumental specular reflections of radiation energy which has been transmitted into said integrating sphere through said radiation energy entry port from striking the interior wall surfaces of the integrating sphere for collection thereby.

6. In an integrating sphere as in claim 5 wherein, said lens means are disposed in said radiation energy exit port.

7. In an integrating sphere as in claim 5 wherein, said lens means are effective to direct said instrumental specular reflections of said radiation energy out of the integrating sphere through said radiation energy entry port.

8. In a spectroscopic quantitative sample analysis system which includes optically aligned radiation energy source, radiation energy integrating sphere having radiation energy entry and exit ports, and a sample analysis cell having a sample viewing window for irradiation of said sample by the transmission of radiation energy from said source through said radiation energy entry and exit ports to impinge on said sample viewing window, the improvements comprising, lens means operatively associated with said radiation energy exit port, said lens means being of positive power and operable to prevent specular reflections from said sample viewing window of radiation energy which has been transmitted from said source through said integrating sphere entry and exit ports from striking the interior wall surfaces of the integrating sphere upon re-entry into the integrating sphere through said radiation energy exit port.

9. In a sample analysis system as in claim 8 wherein, said lens means are disposed in said radiation energy exit port.

10. In a sample analysis system as in claim 8 wherein, said sample viewing window is substantially flat.

11. In a sample analysis system as in claim 8 wherein, said lens means are operable to direct said specular reflections of said radiation energy out of the integrating sphere through said radiation energy entry port.

12. In a sample analysis system as in claim 8 wherein, said lens means are operable to prevent specular reflections from the lens means surfaces of radiation energy from said source which has been transmitted through said radiation energy entry port from striking the interior wall surfaces of the integrating sphere.

13. In a sample analysis system as in claim 12 wherein, said lens means are operable to direct the specular reflections of said radiation energy from the lens means surfaces out of said integrating sphere through said radiation energy entry port.

* * * * *